United States Patent [19]
Werle et al.

[11] Patent Number: 5,183,944
[45] Date of Patent: Feb. 2, 1993

[54] METHOD OF DOPING AQUEOUS SOLUTIONS WITH ACROLEIN IN BIOCIDALLY EFFECTIVE CONCENTRATION

[75] Inventors: Peter Werle; Martin Trageser, both of Gelnhausen-Hoechst; Hermann Piana, Hanau, all of Fed. Rep. of Germany

[73] Assignee: Degussa AG, Frankfurt am Main, Fed. Rep. of Germany

[21] Appl. No.: 798,159

[22] Filed: Nov. 26, 1991

[30] Foreign Application Priority Data

Dec. 3, 1990 [DE] Fed. Rep. of Germany ....... 4038471

[51] Int. Cl.$^5$ .............................................. C07C 45/00
[52] U.S. Cl. ...................................... 568/465; 568/421
[58] Field of Search ................................ 568/421, 465

[56] References Cited

U.S. PATENT DOCUMENTS

| | | | |
|---|---|---|---|
| 3,298,908 | 7/1967 | Newcomer et al. | 514/646 |
| 3,690,857 | 9/1972 | Blair et al. | 71/66 |
| 4,319,047 | 3/1982 | Komora et al. | 568/465 |
| 4,551,560 | 11/1985 | Rizkalla | 568/465 |
| 4,851,583 | 7/1989 | Bockowski et al. | 568/465 |

FOREIGN PATENT DOCUMENTS

| | | | |
|---|---|---|---|
| 603380 | 8/1960 | Canada | 568/465 |
| 0022697 | 1/1981 | European Pat. Off. | 568/465 |

*Primary Examiner*—Werren B. Lone
*Attorney, Agent, or Firm*—Beveridge, DeGrandi & Weilacher

[57] ABSTRACT

Aqueous solutions can be doped in a simple, safe and economic manner with acrolein in biocidally effective concentration by converting acrolein acetals in aqueous phase in the presence of a strongly acidic deacetalation catalyst into acrolein, cleaving the alcohol component, constantly removing the formed acrolein from the decetalation mixture and transferring it by means of an inert gas stream or a liquid jet pump with the aqueous solution to be doped as jet fluid into the aqueous solution to be doped.

16 Claims, No Drawings

METHOD OF DOPING AQUEOUS SOLUTIONS WITH ACROLEIN IN BIOCIDALLY EFFECTIVE CONCENTRATION

BACKGROUND OF THE INVENTION

The present invention relates to a method of doping aqueous solutions, especially water circulation systems, with acrolein in a biocidally effective concentration. In more particular detail, acrolein is formed in the process by means of the deacetalation of open-chain or cyclic acrolein acetals in the presence of strongly acidic catalysts in aqueous phase, is then expelled from this aqueous phase and is transferred into the aqueous solution to be doped.

Acrolein is a well-known biocide for treating liquids, especially aqueous solutions in open and closed circulation systems containing sludge-forming microorganisms; R. Howell et al., Paper Trade Journal 160 (1976), pp. 40-43. The biocidal activity of acrolein is directed to the prevention, regulation and destruction of microorganisms of the type bacteria, viruses, fungi and algae. The high effectiveness of acrolein as a pesticide permits it to be used in a very low concentration of use in water as shown in U.S. Pat. No. 2,959,476 and U.S. Pat. No. 3,250,667.

In spite of the high biocidal effectiveness of acrolein, its dangerous properties limit its ability to be widely used. As a result of its high reactivity, tendency to spontaneously polymerize in an explosive manner when improperly handled, strong irritating action on the respiratory organs and in the eyes as well as its limited storage ability in spite of stabilization, special safety measures are indispensible when acrolein is being handled. These special safety measures require trained personnel which can present a problem. There has therefore been no lack of attempts to use acrolein in the form of a storable and less toxic repository compound, a so-called acrolein splitter, which can be handled in an easier and more reliable manner.

Acroelin acetals can be considered as a depot or repository compound from which acrolein is liberated by means of acid-catalyzed deacetalation as shown in U.S. Pat. No. 4,851,583. Acrolein acetals of lower alcohols such as acrolein dimethyl- and acrolein diethyl acetal are themselves still biocidally active (U.S. Pat. No. 3,298,908; U.S. Pat. No. 3,690,857). However, the handling of these components still involves risks. In contrast thereto, acrolein acetals of longer-chain or polyvalent alcohols are practically ineffective per se as biocides when present in weakly acidic, neutral or weakly basic media, as is customarily done. This is because a splitting off of the acrolein does not take place under these conditions or takes place only to a limited degree. On the other hand, such acetals are almost odorless, relatively non-toxic and can be handled without significant problems.

French patent 1,546,472 describes a method of purifying glycerol containing cyclic acrolein glycerol acetals. In this method, a treatment with acidic ion exchangers takes place, followed by such a treatment with anion exchangers doped with hydrogen sulfite groups. The deacetalation for the purpose of obtaining acrolein and doping aqueous solution is not disclosed.

According to the method of U.S. Pat. No. 4,851,583, acrolein acetals of the general formula

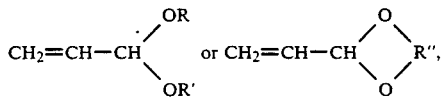

in which R and R' signify a $C_1$— to $C_6$—alkyl group and R" is the residue of a bi- or polyvalent alcohol, e.g. of a 1,2-glycol or glycerol, are split or cleaved using strongly acidic ion exchangers. The use of mineral acids is presented in this prior patent as unsatisfactory. The solutions obtained during the deacetalation, which contain acrolein and the alcohol and are therefore effective as pesticide, are used to treat water. In a repetition of example 2 of U.S. Pat. No. 4,851,583 using the non-toxic acrolein glycerol acetal (a mixture of cis- and trans-2-vinyl-4-hydroxymethyl-1,3-dioxolane and cis- and trans-2-vinyl-5-hydroxy-1,3-dioxane) it was found that in the time indicated, only approximately 40% of the acetal was cleaved. Therefore, the previously known method has the following disadvantages:

- The incomplete utilization of the acetal used, which considerably reduces its economy for use as a biocide;
- The low concentration of acrolein acetal used (0.1-0.16% by weight);
- The very large amount of ion exchanger relative to acrolein acetal used;
- The use of very expensive, perfluorinated ion exchanger with sulfonate groups;
- The transfer of even the alcohol of the acrolein acetal into the water to be biocidally treated, thus increasing the content of organic matter in the water.

SUMMARY OF THE INVENTION

An object of the present invention is to provide a method of doping aqueous solutions with acrolein in biocidally effective concentration which does not have the disadvantages of the previously known method.

In attaining the above and other objects, a feature of the present invention resides in a method for doping aqueous solutions with acrolein in a biocidally effective concentration in which the acrolein is formed by means of the deacetalation reaction of acrolein acetals in aqueous phase in a reaction system in the presence of a strongly acidic catalyst. In carrying out the method of the invention, the acrolein formed during the deacetalation reaction is constantly removed from said aqueous phase of the reaction system and transferred over into the aqueous solution to be doped. More specifically, an inert gas stream is first conducted through said aqueous phase in the reaction system and becomes thereby doped with acrolein and is then introduced into the aqueous solution to be doped. In this step the acrolein is dissolved out of the gas stream and is introduced into the aqueous solution to be doped. Alternatively, the pressure can be lowered over the aqueous phase reaction system using a liquid jet pump whose motive fluid is the aqueous solution to be doped or the water to be added to it. The drawn off acrolein dissolves in this water, and, to the extent necessary, the motive fluid doped with acrolein is mixed with the aqueous solution to be doped.

DETAILED DESCRIPTION OF THE INVENTION

The acrolein acetals to be used in accordance with the invention are open-chain and cyclic acetals like those known from U.S. Pat. No. 4,851,583, the disclosure of which is relied on and incorporated herein. Those acrolein acetals are preferably used whose alcohol component boils sufficiently far, thus at least 20° C., preferably over 40° C. above the boiling point of acrolein. Among the monovalent alcohols, primary alcohols with 3 to 5 C atoms are preferred. Alcohols with 2 and more hydroxyl groups, especially 2 and 3 OH groups, preferably contain 2 to 6 C atoms. 1,2- and 1,3-diols with 2 to 4 C atoms, triols of the glycerol and trimethylolethane or -propane type as well as pentaerythritol are preferred as alcohol components for cyclic acrolein acetals with a 1,3-dioxolane-or 1,3-dioxane ring structure. Mixtures of acrolein acetals can also be used, e.g. those which are obtainable from the acetalation of acrolein with glycerol. The preparation of the acetals is known, see U.S. Pat. No. 3,014,924. It is advantageous to use acrolein acetals with as low a toxicity as possible as the source for acrolein. This includes e.g. the cyclic acrolein glycerol acetals.

The deacetalation can be carried out in aqueous phase at temperatures in a range of 0° to 100° C., but preferably at 10° to 50° C. and especially at 20° to 40° C. The formation of acrolein is accelerated at a higher temperature but at the same time undesired side reactions can occur which lead to a loss of acrolein available for the doping.

The deacetalation is catalyzed by strongly acidic catalysts. The acid can be used in solid form or in dissolved form. Among the acids in dissolved form, mineral acids such as especially sulfuric acid and phosphoric acid, moreover strong organic acids such as sulfonic acids and perfluorinated carboxylic acids are well suited. The strong acids named can also be bound to solid carriers such as e.g. silicas and silicates. The acids in solid form are preferably strongly acidic organic and inorganic ion exchangers, especially exchange resins which contain sulfonate groups and are based on a styrene/-divinyl benzene polymer matrix or on a polymeric organosiloxane (See DE patents 32 26 093 and 35 18 881). It is clear that the speed of the liberation of acrolein during deacetalation can be increased by lowering the weight ratio of acrolein acetal to catalyst.

Whereas the use of a very expensive ion exchanger in a large amount was required according to the previously known method for deacetalation—1 g Nafion resin per 67 mg acrolein diethyl acetal in 40 ml water according to example 2 of U.S. Pat. No. 4,851,583—acids of any desired strength are able to be used in a lesser amount according to the present invention. It is important that the acrolein formed is removed if possible immediately after its formation from the aqueous phase reaction system of the deacetalation mixture. It is possible in this manner to liberate acrolein almost quantitatively from the acetal and to transfer it into the aqueous solution to be doped. An aqueous solution of the alcohol component of the acetal remains in the deacetalation reactor after the complete deacetalation and removal of the acrolein. Amounts of the alcohol can only be co-transferred into the solution to be doped in the case of alcohols with a low boiling point, e.g. ethanol and propanol.

The transfer of the liberated acrolein into the aqueous solution to be doped with it can be brought about without problems by conducting an inert gas stream, especially nitrogen or air, through the aqueous phase of the deacetalation mixture. The gas stream picks up the acrolein thereby and releases it into the aqueous solution to be doped when the gas stream is introduced into said solution. The gas stream can be passed through, which also includes a suction through of the gas stream, at normal pressure or at reduced pressure.

According to an alternative embodiment, the acrolein is transferred under reduced pressure from the deacetalation reactor into the solution to be doped using a liquid jet pump. The liquid jet pump of a customary design such as e.g. so-called water jet pumps is preferably operated with the aqueous solution to be doped as pumping jet. The acrolein thus dissolves immediately into the motivating jet. The motivating jet doped with acrolein is mixed, if necessary, with solution which is undoped or insufficiently doped in order to adjust or maintain the desired degree of doping. Such pumps are known in the art, as shown for example in Ullmanns Enzyklopaedie der Technischen Chemie, Vol. I (1951) pp. 47, 130, 131.

The method of the invention can be used to treat open or closed water systems. Circulation systems with large amounts of water are found among other places in power plants, refineries, in the paper industry, kaolin industry and in exploration activities for petroleum or natural gas. The suitable, biocidally effective concentration of acrolein is customarily in a range of 5 to 10 ppm. In general, acrolein must be dosed in such a manner that on the one hand a sufficient biocidal source action remains over a fairly long time period but on the other hand no problems are caused by acrolein.

The special and non-foreseeable advantage of the method of the invention resides in the fact that it is possible to carry out the doping as needed in a reliable manner and with low technical expense utilizing the acetal used in a practically quantitative manner. The reactor size for the deacetalation is adapted to the amount of water to be doped and to the desired degree of doping. The acrolein acetal can be used in any desired concentration up to 50% in water, so that generally only small reactors are required. As has already been explained, the amount of acrolein formed per unit of time can be controlled in a simple manner via the weight ratio of acetal to catalyst, even in the case of a given amount of acetal.

COMPARATIVE EXAMPLE

In accordance with example 2 of U.S. Pat. No. 4,851,853, 100 ml of a 0.17% by weight solution of acrolein glycerol acetals in deionized water was compounded with 2.5 g Nafion 471 and agitated 15 minutes at 20° C.

The solution was then analyzed with gas chromatography. 0.029 g acrolein and 0.101 g acrolein glycerol acetals were confirmed in the solution, which is 39.6% of theory yield of acrolein and still 59.4% of the amount of acrolein glycerol acetals used. The precision of the measuring methods is ±3%.

EXAMPLE 1

500 g of a 10% by weight aqueous acrolein glycerol acetal solution are compounded with 10 g moist ion exchanger of the type Lewatit SC 104 (H+ form) (Bayer AG). The reaction vessel is heated to 40° C. and a water jet pump vacuum put on it. The majority of the acrolein formed distills off thereby and the pressure is adjusted to approximately 100 mbars after 15 minutes. During the course of 30 minutes, the pressure drops further to approximately 60 to 70 mbars. The distilled-off acrolein-water mixture is caught in a trap cooled with liquid nitrogen and determined, after having been diluted with water, by gas chromatography. 20.0 g acrolein were found; that corresponds to approximately 93% of theory. the flask itself contained glycerol in addition to traces of acrolein glycerol acetal.

EXAMPLE 2

400 g of a 20% by weight aqueous acrolein glycerol acetal solution are compounded with 3 ml 96% by weight sulfuric acid. A stream of nitrogen of approximately 0.5 l/min. is conducted through the solution heated to 50° C. and the acrolein formed thereby is expelled. The reaction is broken off after 1.5 hours. An acrolein portion of 32.5 g was found in the deep-cooled receiver by gas chromatography. Acrolein glycerol acetal could still be confirmed at about 0.5% in the deacetalation flask by gas chromatography.

EXAMPLE 3

Doping of 20 m$^3$ Water Circulation System 1160 g of a 20% by weight aqueous acrolein glycerol acetal solution were placed in a 2 liter reaction vessel at 20° C., compounded with 45 g moist ion exchanger of the Lewatit SC 104 type (H$^+$ form) and the forming acrolein drawn off in the course of 1.5 hours at 40° C. interior temperature with simultaneous lowering of the pressure by means of a water jet pump to approximately 60 to 70 mbars in gaseous form into the water jet pump.

The water jet pump was operated with a water stream of the 20 m$^3$ water circulation system to be doped with a value of 6.8 on the pressure side with 5 bars and the pump discharge, in which the gaseous acrolein- and acrolein-water mixtures removed by suction had dissolved, returned to the water circulation system.

After termination of the doping, an acrolein content of 4.5 ppm was measured in the cooling water system by means of a photometric analysis method (color reaction with dinitrophenylhydrazine).

0.4% by weight acrolein glycerol acetal was also found in addition to glycerol as the main component in the bottom of the reaction vessel by gas chromatography.

Further variations and modifications will be apparent to those skilled in the art and are intended to be encompassed by the claims appended hereto.

German priority Application No. P 40 38 471.3 is relied on and incorporated by reference.

We claim:

1. A method for doping aqueous solutions with acrolein in biocidally effective concentration, said method comprising
   (a) forming acrolein by deacetalization of acrolein acetal in aqueous phase with a strongly acidic catalyst,
   (b) removing acrolein formed during said deacetalization from said aqueous phase, and
   (c) transferring said acrolein into an aqueous solution to be doped by (I) conducting an inert gas stream through said aqueous phase to become doped with acrolein and introducing said gas stream into said aqueous solution to be doped, dissolving said acrolein out of said gas stream into said aqueous solution; or (II) by lowering the pressure over said aqueous phase using a liquid jet pump whose motive fluid is the aqueous solution to be doped or water to be added to it, in which the drawn off acrolein dissolves.

2. The method according to claim 1, wherein the acrolein acetal is an acrolein di-n-alkyl acetal whose alkyl groups contain 3 to 5 C atoms, or a cyclic acrolein acetal whose alcohol component contains 2 to 6 C atoms and 2 to 6 OH groups.

3. The method according to claim 2 wherein said alcohol component contains 2 to 4 OH groups.

4. The method according to claim 1, wherein a strongly acidic inorganic or organic ion exchanger is used as deacetalation catalyst.

5. The method according to claim 4 wherein said exchange resin contains sulfonate groups and is based on a styrene/divinyl benzene polymer matrix or polymeric organosiloxane.

6. The method according to claim 1, wherein a mineral acid is used as a deacetalation catalyst.

7. The method according to claim 6 wherein said acid is sulfuric acid.

8. The method according to claim 1, wherein said deacetalization occurs at a temperature from 0° C. to 100° C.

9. The method according to claim 8, wherein said temperature is 10° C. to 50° C.

10. The method according to claim 9, wherein said temperature is 20° C. to 40° C.

11. A method for doping aqueous solutions with acrolein in biocidally effective concentration, said method comprising
   (a) reacting acrolein acetal with a strongly acidic catalyst in aqueous phase in a deacetalization reactor at a temperature from 0° C. to 100° C. to form alcohol and acrolein, wherein the alcohol component of said acrolein acetal is an alcohol whose boiling point is at least 20° C. above the boiling point of acrolein acetal, wherein said strongly acidic catalyst is selected from the group consisting of sulfuric acid, phosphoric acid, sulfonic and perfluorinated carboxylic acids or said strongly acidic catalyst is an exchange resin containing sulfonate groups and is based on a styrene/-divinyl benzene polymer matrix or on a polymeric organosiloxane;
   (b) removing said acrolein from said aqueous phase, and
   (c) transferring said acrolein into an aqueous solution to be doped by (I) conducting an inert gas stream through said aqueous phase to become doped with acrolein and introducing said gas stream into said aqueous solution to be doped, dissolving said acrolein out of said gas stream into said aqueous solution; or (II) by lowering the pressure over said aqueous phase using a liquid jet pump whose motive fluid is the aqueous solution to be doped or water to be added to it, in which the drawn off acrolein dissolves.

12. The method according to claim 1, wherein said alcohol component is a monovalent primary alcohol with 3 to 5 carbon atoms.

13. The method according to claim 1, wherein said alcohol component is an alcohol with at least 2 hydroxyl groups.

14. The method according to claim 13, wherein said alcohol is a 1,2- or 1,3-diol with 2 to 4 carbons atoms, glycerol, trimethylolethane, trimethylolpropane or pentaerythritol.

15. The method according to claim 1, further comprising admixing the motive fluid doped with acrolein to the aqueous solution to be doped.

16. The method according to claim 11, further comprising admixing the motive fluid doped with acrolein to the aqueous solution to be doped.

* * * * *